United States Patent [19]

Fard

[11] Patent Number: 5,645,546
[45] Date of Patent: Jul. 8, 1997

[54] BONE SCREW AND SCREW DRIVER BLADE SYSTEM FOR ORAL AND MAXILLOFACIAL SURGICAL PROCEDURES

[75] Inventor: Mike M. Fard, Santa Ana, Calif.

[73] Assignee: MicroAire Surgical Instruments, Valencia, Calif.

[21] Appl. No.: 396,534

[22] Filed: Apr. 3, 1995

Related U.S. Application Data

[63] Continuation of Ser. No. 944,777, Sep. 14, 1992, abandoned.

[51] Int. Cl.[6] .................................................. A61B 17/56
[52] U.S. Cl. ............................. 606/72; 606/73; 606/104
[58] Field of Search .............................. 606/65, 72–78; 411/402, 403, 404, 410; 81/436, 451

[56] References Cited

U.S. PATENT DOCUMENTS

| | | | |
|---|---|---|---|
| 2,173,707 | 9/1939 | Brown | 411/403 |
| 2,400,684 | 5/1946 | Clark | 411/403 |
| 3,175,543 | 3/1965 | Launay | 411/403 |
| 3,424,212 | 1/1969 | Kemper | 411/403 |
| 3,449,988 | 6/1969 | Gallo | 81/451 |
| 4,325,153 | 4/1982 | Finnegan | 411/403 |
| 4,452,556 | 6/1984 | Nelson | 411/403 |
| 4,754,749 | 7/1988 | Tsou | 411/403 |
| 4,936,728 | 6/1990 | Sainsbury | 411/403 |
| 5,122,132 | 6/1992 | Bremer | 606/76 |

FOREIGN PATENT DOCUMENTS

| | | | |
|---|---|---|---|
| 0451932 | 10/1991 | European Pat. Off. | 606/73 |

*Primary Examiner*—Michael A. Brown
*Attorney, Agent, or Firm*—Whitham, Curtis, Whitham & McGinn

[57] ABSTRACT

A titanium bone screw has a centering hole located in the midpoint of the slot in the screw head. A screw driver blade with a centering pin is so dimensioned that the blade and tip respectively form interference fit with the slot and centering hole when the blade is inserted into the screw head.

11 Claims, 1 Drawing Sheet

BONE SCREW AND SCREW DRIVER BLADE SYSTEM FOR ORAL AND MAXILLOFACIAL SURGICAL PROCEDURES

This application is a continuation of application Ser. No. 07/944,777 filed Sep. 14, 1992 now abandoned.

BACKGROUND OF THE INVENTION

1. Field of the Invention

This invention relates to plate and bone screw systems for permanently fixating facial bones with respect to one another. More particularly, it relates to an improved screw and screw driver in which the screw driver holds the screw firmly and precisely, allowing the surgeon to pick up the screw and position it with one hand.

2. Description of the Prior Art

As will be appreciated by those skilled in the art, plates and screws used in oral and maxillofacial surgery are advantageously made of titanium. Such components have high strength, yet can be easily shaped to the bone contour. They are bio-compatible, chemically inert and non-corrosive. Titanium plates exhibit minimum rebound after bending, resulting in stable fracture and osteotomy sites. In addition, titanium plates and screws are non-magnetic.

In a facial plating system for permanent fixation of facial bones, the plates are placed on a fracture site and fastened to the bone using the bone screw. A surgeon typically uses one hand for accurate placement of the plate, leaving only one hand to pick up and place the screw in the right location. In such a one-handed pick-up and position procedure, it is critically important that the screw driver provide unassisted screw pick-up and securely hold the screw for accurate placement.

SUMMARY OF THE INVENTION

An object of this invention is the provision of a bone screw and screw driver combination for single-handed use by surgeons performing oral and maxillofacial surgery.

Briefly, this invention contemplates the provision of a titanium bone screw with a centering hole located in the midpoint of the slot in the screw head. A screw driver blade with a centering pin is so dimensioned that the blade and tip respectively form interference fit with the slot and centering hole when the blade is inserted into the screw head.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
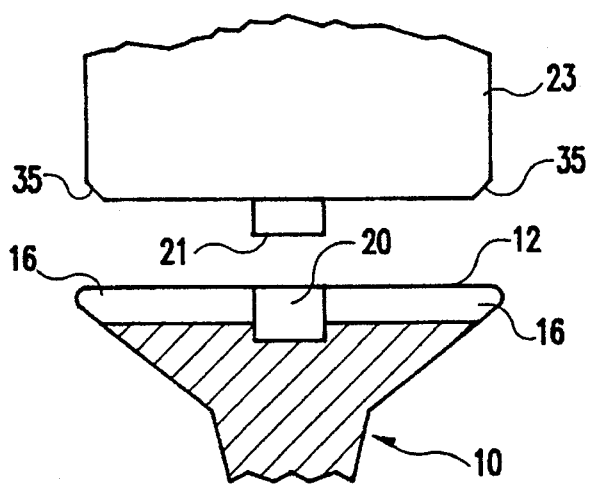
FIG. 1 is a fragmented side view, with parts in section, of a screw driver blade and bone screw in accordance with the teachings of this invention.
Figure 2:
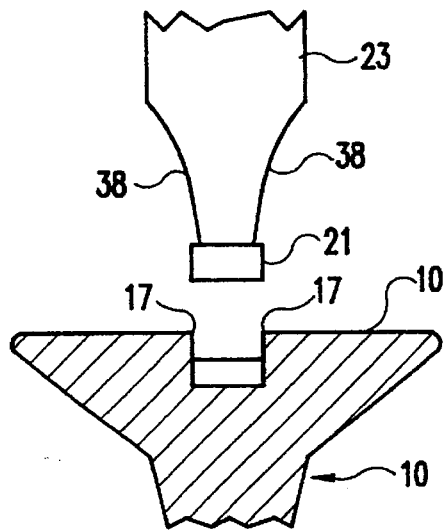
FIG. 2 is an end view of the combination shown in FIG. 1.
Figure 3:
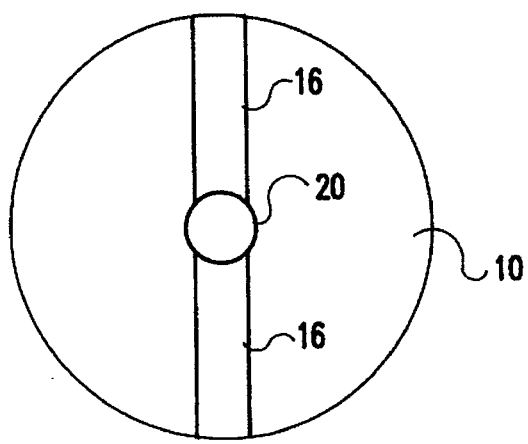
FIG. 3 is a plan view of the screw head.

Referring now to FIGS. 1, 2, 3, and 4, a bone screw 10 in accordance with the teachings of this invention, is preferably made of titanium and is self-tapping with triple radial flutes for maximum tapping effectiveness and to assure straight alignment. The upper surface 12 of the head of the screw is flat and the head fits the facial plate so that upper surface 12 is substantially flush with the surface of the plate when the screw is in place.

A slot 16 extends across the head of the screw. The walls of the slot 16 are parallel to one another and are perpendicular to the bottom of the slot.

A shallow cylindrical hole 20, in the center of the slot 16, is dimensioned to provide an interference fit with a cylindrical pin 21 on the screw driver blade 23 in order to both center the bone screw 10 on the blade and to hold it firmly in place. The wall of the cylindrical is perpendicular to the upper surface 12 of the screw head. In this preferred embodiment of the invention, the hole diameter and the pin diameter are slightly wider than the slot.

The blade 23, is designed and dimensioned so that, when the blade is in place in the slot 16, in addition to an interference fit between pin 21 and hole 20, there is also an interference fit between the top edges 17 of the slot 16 and the sides of the blade.

Figure 5:
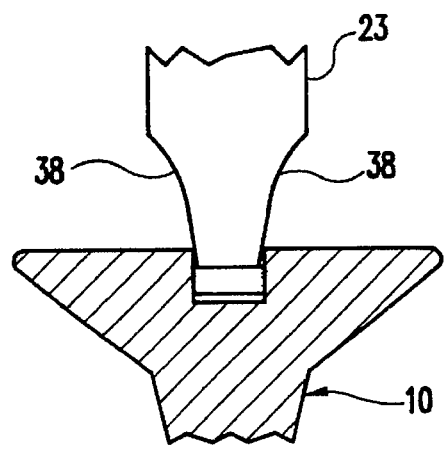
FIG. 5 shows the blade fully engaged with the screw head.
Figure 4:
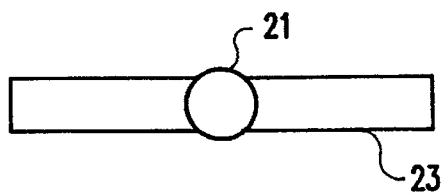
FIG. 4 is a plan view of the blade.
Figure 6:
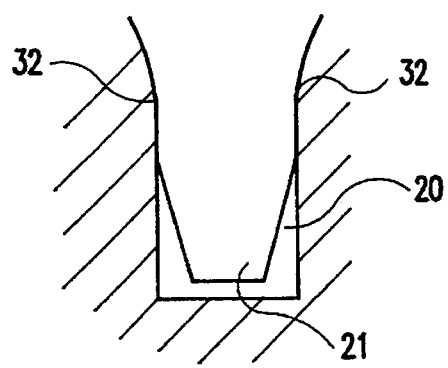
FIG. 6 is a fragmented detail view of a blade pin seated in a centering hole.

Referring now to FIGS. 5 and 6 in addition to FIGS. 1–4, the side walls of the pin 21 taper slightly outward (e.g., about 2 degrees) from the bottom of the pin to a flat surface region 32 on each side wall. The distance between the flat surfaces is such as will provide an interference fit between the flat surfaces 32 and the side walls of the recess 20. As will be appreciated by those skilled in the art, interference fit, or more precisely, locational interference fits are defined by ANSI both functionally and in tables that prescribe the fit for any given size, or type of fit, and also prescribe the standard limits for the mating parts which will produce the fit. Table 5 of the ANSI Standard Fits sets forth the ANSI Standard Interference Locational Fits (ANSI B-1-1967, R1974). In general, for the size parts contemplated here, an interference fit is achieved when the dimensions of the parts overlap in a range from about 0.008 to 0.0006 inches.

The side wall surfaces 38 of the screw driver blade curve outwardly from the bottom of the blade. The blade increases from a thickness at the bottom of the blade that is less than the width of the slot 16, to a thickness at the top edge of the slot 16 that forms an interference fit between the edges of the slot and the blade.

In an operation, a surgeon picks up a screw by merely inserting the blade into the screw slot until the bottom of the blade contacts the bottom of the slot. At this position, there is an interference fit between the flat surfaces 32 on the pin 21 and the side walls of the hole 20. In addition, there is an interference fit between the top edges of the slot 16 and the curved side wall surfaces of the blade 23. Preferably, there is a close fit between the remaining two sides of the pin 21 and the corresponding walls of the hole 20 so that the blade is accurately centered with respect to the screw. As indicated in FIG. 5, there is a small clearance between the bottom of the pin 21 and the bottom of the hole 20.

After the surgeon has positioned the screw, he or she can screw it into the bone, still using one hand. To remove the blade from the screw after it has been inserted into the bone, the surgeon need only to rock the blade gently from side to side along the length of the slot, breaking the interference fit between the screw and the blade. Here, it should be noted that in this preferred embodiment the pin is sufficiently short to allow this rocking motion in freeing the blade from the bone screw. Further, to facilitate this rocking motion, the ends 35 of the blade may be slightly beveled.

While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. A bone screw and screw driver blade adapted in combination to allow a surgeon using only one hand to pick up said bone screw with said blade, insert said bone screw into a bone, and release said bone screw from said blade, comprising in combination:

a screw slot having opposing side walls, spaced apart by a first predetermined distance, and a bottom wall surface in said bone screw;

a recess extending into said bone screw from said bottom wall surface, said recess forming in said screw opposing wall surfaces that are spaced apart from one another by a first predetermined dimension, said first predetermined dimension being larger than said first predetermined distance;

a screw driver blade having a bottom surface and side walls extending from said bottom wall surface that are spaced apart from one another by a second predetermined distance;

a pin on said screw driver blade extending from said bottom surface, said pin having opposing wall surfaces that are spaced apart from one another by a second predetermined dimension that is larger than said second predetermined distance;

said pin and said recess each so dimensioned, one relative to the other, so that said second predetermined dimension and said first predetermined dimension overlap by an amount such that when said pin is inserted into said recess there is an interference fit between said pin and said recess.

2. A bone screw and a screw driver blade as in claim 1, wherein said bone screw is made of titanium.

3. A bone screw and a screw driver blade as in claim 1, wherein said screw slot opposing side walls having facing parallel top edges separated by a gap of a third predetermined dimension and said screw driver blade sidewalls are spaced apart by a fourth predetermined dimension and are so dimensioned, one relative to the other, that said gap dimension and screw driver blade dimension overlap, whereby when said screw driver blade is inserted into said screw slot and said screw driver blade bottom surface engages said screw slot bottom wall surface, there is an interference fit between said top edges and said screw driver blade.

4. A bone screw and screw driver blade adapted in combination to allow a surgeon using only one hand to pick up said bone screw with said blade, insert said bone screw into a bone, and release said bone screw from said screw driver blade, comprising:

a bone screw having a bone contacting end and a screw driving end, said screw driving end having a screw slot with opposing side walls spaced apart by a first dimension, a bottom wall positioned between said opposing side walls, and a cylindrical recess having a diameter of a second dimension that is larger than said first dimension positioned in said screw slot and extending to a point in said bone screw below said bottom wall of said screw slot; and a screw driver blade which fits within said screw slot of said bone screw, said screw driver blade having side walls spaced apart by a third dimension that is large enough to form an interference fit with said opposing side walls of said screw slot which are spaced apart by said first dimension, said screw driver blade having a cylindrical pin extending from a bottom surface, said cylindrical pin having a pin diameter of a fourth dimension that is large enough to form an interference fit with said cylindrical recess in said bone screw which has said diameter of said second dimension.

5. A bone screw and screw driver blade adapted in combination to allow a surgeon using only one hand to pick up said bone screw with said blade, insert said bone screw into bone, and release said bone screw from said blade, comprising in combination:

a screw slot having opposing side walls and a flat bottom wall surface in said bone screw;

a cylindrical recess extending into said bone screw from said flat bottom wall surface, said cylindrical recess having a first predetermined diameter;

a screw driver blade having a flat bottom surface and side walls extending from said flat bottom surface and defining a first predetermined distance between said side walls;

a cylindrical pin on said screw driver blade extending from said flat bottom surface, said cylindrical pin having a second predetermined diameter that is larger than said first predetermined distance;

said second predetermined diameter and said first predetermined diameter each so dimensioned, one relative to the other, that said second predetermined diameter and said first predetermined diameter overlap by an amount such that when said cylindrical pin is inserted into said cylindrical recess there is an interference fit between said cylindrical pin and said cylindrical recess.

6. A bone screw and a screw driver blade as in claim 5, wherein said screw slot opposing side walls having facing parallel top edges separated by a gap of a third predetermined dimension and said screw driver blade sidewalls are spaced apart by a fourth predetermined dimension and are so dimensioned, one relative to the other, that said gap dimension and screw driver blade dimension overlap, whereby when said screw driver blade is inserted into said screw slot and said screw driver blade bottom surface engages said screw slot bottom wall surface, there is an interference fit between said top edges and said screw driver blade.

7. A bone screw and screw driver blade as in claim 6, wherein said cylindrical pin is tapered at its end remote from said bottom surface.

8. A bone screw and screw driver blade as in claim 6, wherein said overlap is in a range from approximately 0.008 inches to 0.006 inches.

9. A bone screw and screw driver blade as in claim 5, wherein said cylindrical pin is tapered at its end remote from said bottom surface.

10. A bone screw and screw driver blade as in claim 5, wherein said overlap is in a range from approximately 0.008 inches to 0.006 inches.

11. A bone screw and a screw driver blade adapted blade adapted in combination to allow a surgeon using only one hand to pick up said bone screw with said blade, insert said bone screw into a bone, and release said bone screw from said screw driver blade, comprising:

a bone screw having a bone contacting end and a screw driving end, said screw driving end having a screw slot with opposing side walls spaced apart by a first dimension, a bottom wall positioned between said opposing side walls, and a cylindrical recess having a diameter of a second dimension positioned in said screw slot and extending to a point in said bone screw below said bottom wall of said screw slot;

and a screw driver blade which fits within said screw slot of said bone screw, said screw driver blade having side walls spaced apart by a third dimension that is large enough to form an interference fit with said opposing side walls of said screw slot which are spaced apart by said first dimension, said screw driver blade having a cylindrical pin extending from a bottom surface, said cylindrical pin having a pin diameter of a fourth dimension that is larger than said third dimension and large enough to form an interference fit with said cylindrical recess in said bone screw which has said diameter of said diameter of said second dimension.

* * * * *